US006920781B2

(12) United States Patent
Olesen

(10) Patent No.: US 6,920,781 B2
(45) Date of Patent: Jul. 26, 2005

(54) GRAVIMETRIC MOISTURE-DETERMINATION INSTRUMENT WITH AN AIR DUCT FOR COOLING

(75) Inventor: Neil Olesen, Millington, NJ (US)

(73) Assignee: Mettler-Toledo GmbH, Greifensee (CH)

( * ) Notice: Subject to any disclaimer, the term of this patent is extended or adjusted under 35 U.S.C. 154(b) by 13 days.

(21) Appl. No.: 10/646,201

(22) Filed: Aug. 21, 2003

(65) Prior Publication Data

US 2004/0103718 A1 Jun. 3, 2004

Related U.S. Application Data

(63) Continuation of application No. 09/851,004, filed on May 7, 2001, now abandoned.

(30) Foreign Application Priority Data

May 8, 2000 (DE) .......................................... 100 22 099

(51) Int. Cl.[7] ........................... G01N 25/56; F26B 25/06
(52) U.S. Cl. ...................... 73/73; 73/75; 73/76; 34/226
(58) Field of Search ................................ 73/73, 75, 76

(56) References Cited

U.S. PATENT DOCUMENTS 3,664,181 A * 5/1972 Conrad et al. ................ 73/571
4,465,152 A * 8/1984 Schmitter .................... 177/180
4,703,151 A * 10/1987 Sakamoto .................... 219/518
4,771,631 A * 9/1988 Lehtikoski et al. ............ 73/73
5,392,631 A * 2/1995 Elwell .......................... 73/1.79
5,485,684 A * 1/1996 Philipp et al. ................ 34/226
5,499,532 A * 3/1996 Kaiho et al. .................... 73/76
5,513,538 A * 5/1996 Baker et al. ................ 73/865.6
5,617,648 A * 4/1997 Leisinger et al. ............. 34/226
5,787,600 A * 8/1998 Leisinger et al. .............. 34/89
5,826,498 A * 10/1998 Su .............................. 99/476
5,878,508 A * 3/1999 Knoll et al. .................. 34/488
5,950,526 A * 9/1999 Hsu ............................. 99/476

* cited by examiner

Primary Examiner—Hezron Williams
Assistant Examiner—Katina Wilson
(74) Attorney, Agent, or Firm—Friedrich Kueffner

(57) ABSTRACT

A gravimetric moisture-determination instrument which is cooled by an air stream includes a housing containing a balance and a radiant heater. The moisture content of a sample placed on the balance pan is determined by measuring the weight loss of the sample while it is being dried under the heater. The gravimetric moisture-determination instrument further includes a heat source located above the balance for heating the sample in order to evaporate the moisture from the sample, so that the moisture content can be determined from the weight loss of the sample. Between the heat source and the weighing cell of the balance, the instrument contains a device for conducting an air stream.

10 Claims, 2 Drawing Sheets

GRAVIMETRIC MOISTURE-DETERMINATION INSTRUMENT WITH AN AIR DUCT FOR COOLING

CROSS REFERENCE TO RELATED APPLICATIONS

This application is a continuation application of U.S. patent application Ser. No. 09/851,004 filed May 7, 2001, now abandoned.

BACKGROUND OF THE INVENTION

The invention relates to a gravimetric moisture-determination instrument that is cooled by an air stream. In essence, the instrument consists of a housing containing a balance and a radiant heater. The moisture content of a sample placed on the balance pan is determined by measuring the weight loss of the sample while it is being dried under the heater.

Instruments for the gravimetric determination of moisture content are known and commercially available. They share as a common operating principle that a sample whose moisture content is to be determined is placed on a balance that continuously monitors the weight of the sample while the latter is being heated, normally by a conventional infrared radiator or halogen radiator. As a result of the heating, moisture is evaporated from the sample, which causes a weight loss that is measured by the balance. A variety of arrangements are used for placing the sample into the moisture-determination instrument. In one arrangement, the entire balance including the weighing pan slides in and out of the housing. In another arrangement, the balance is installed in a fixed position in the housing while the heater can slide or swivel out of the way. In a third category of instruments, the heater is installed in a hinged top cover of the instrument, and the sample pan is made accessible by tilting up the cover of the instrument housing.

The balance, and especially the weighing cell of the balance, can be protected from heating up, if the instrument is equipped with a means for conducting an air stream through a space between the balance pan and the pan-supporting part of the weighing cell, as described in the Swiss patent application CH-A-689650. To achieve a thermal separation between the hot portions of the moisture-determination instrument and the weighing cell, ambient air is blown through a wide air duct below the weighing pan, for example by a fan installed in the housing of the instrument. To clean the air before running it through the cooling duct, the arrangement may also include a filter pad at the intake opening. The moisture-determination instrument as described in the aforementioned reference has a housing with a drawer holding a precision balance. To place the sample on the balance, the drawer is pulled out, and to perform the measurement, the drawer is pushed in. The means for conducting an air stream, e.g., an air duct, is preferably configured so that it slides in and out of the housing together with the balance. The air duct is divided into two sections, one of which is installed in the part of the moisture-determination instrument that contains the heater, while the other section is connected to the balance.

If the moisture-determination instrument of the foregoing description is used in a dusty or exceptionally dirty environment, there is a risk that the dust particles from the ambient air may clog up the filter pad in a very short time, so that filter pads have to be replaced on a frequent or even daily basis. The problem with replacing the filter pads is that users may neglect to do it, particularly if the filter pad is set in a holder that is complicated to unscrew, as is the case with commercially available moisture-determination instruments of the kind where the balance is fixed in the housing and the heater is movably mounted above the balance. If the filter pad is not replaced when needed, the clogged-up filter will obstruct the passage of air, so that the instrument is no longer cooled properly.

Although it is conceivable to use the instrument without the filter pad, this will over time lead to an accumulation of dust in the air duct which can make the cooling action less effective. This can make it necessary to clean the air duct from time to time in a complicated procedure requiring a partial disassembly of the instrument.

OBJECTIVE AND SUMMARY OF THE INVENTION

In a gravimetric moisture-determination instrument equipped with an air duct between the balance pan, the weighing cell, and a pan-supporting load-receiver that is attached to the weighing cell, the present invention aims to improve the design of the air duct so that the latter can be cleaned in a simple routine procedure.

The invention solves this problem by proposing an arrangement where at least a part of the air duct is removable from the housing for cleaning. The gravimetric moisture-determination instrument according to the invention consists of a balance installed in a housing, as well as a heat source located above the balance, which heats the sample to evaporate the moisture from it, so that the moisture content can be determined from the weight loss of the sample. Between the heat source and the weighing cell of the balance, more specifically between the balance pan (or sample tray) and the weighing cell, the instrument contains means for conducting an air stream, e.g., propelled by a cooling fan. The air-conducting means include an air duct that can be released from the housing in a simple way for cleaning. The invention has the advantage that it eliminates the complicated and—after a time—expensive replacement of filter pads and, in addition, that the aforementioned cleaning procedure has to be performed less frequently than the filter replacement. If the ventilating means require cleaning at all, which may happen in the case of a very dusty environment, the cleaning procedure can easily be done by the user, so that it will not be necessary to call in a service technician to disassemble and clean the air duct.

The air duct can be configured as a single part or in more than one part, but is preferably dimensioned to cover the entire length and width of the weighing cell. At least, there has to be some kind of provision for removing the heat from an area above the entire length and width of the weighing cell. The specific configuration of the air duct or the provision for heat removal depends on the design of the balance. In the aforementioned moisture-determination instrument where the balance is set in a pull-out drawer, the ventilation means or general provisions for cooling could be configured to slide out of the housing together with the balance. All solutions according to the invention have in common that either the entire ventilation means can be removed from the instrument for cleaning, or that the ventilation means has a removable top cover, and that the removal requires opening of no more than a few fasteners, preferably only a single fastener such as a screw or a snap-locking toggle device.

In a preferred embodiment of the invention, the air duct is configured as a wide corridor passing across the top of the housing, where the upper surface of the housing represents the bottom of the corridor and an upper shell forms the ceiling of the corridor. The upper shell is attached to the bottom of the air corridor, i.e., to the instrument housing, by only one fastener that is located in a conveniently accessible place. Alternatively, the upper shell could also be hinged on the instrument housing so as to open to the front or the side, or the upper shell could slide out to the front. In this case, too, the upper shell could be secured by a screw or a snap-locking mechanism engaged in a mating counterpart in the bottom of the corridor.

In a further embodiment, the air duct is designed as an integral, one-piece duct unit attached to the top of the instrument housing, e.g., by a screw that passes through the duct unit from above and is anchored in the top of the instrument housing. Here, too, it is conceivable to use a snap-locking mechanism. The air-conducting means can also be designed so that a branch of the air duct runs near the balance electronics, so that the latter will likewise be cooled.

In a further developed embodiment of the invention, the air duct is not limited to a horizontally extending chamber between an upper shell and the top of the instrument housing, but also reaches downward over the sides of the instrument housing as an inverted U-profile where the air duct can form a part of the housing.

A preferred embodiment of the air-conducting means will be discussed in more detail based on an example illustrated in the following drawings. Schematically simplified and reduced to the essential features of the invention, the drawings represent a moisture determination instrument with a heat source integrated in a hinged top cover.

DESCRIPTION OF PREFERRED EMBODIMENTS

Figure 1:
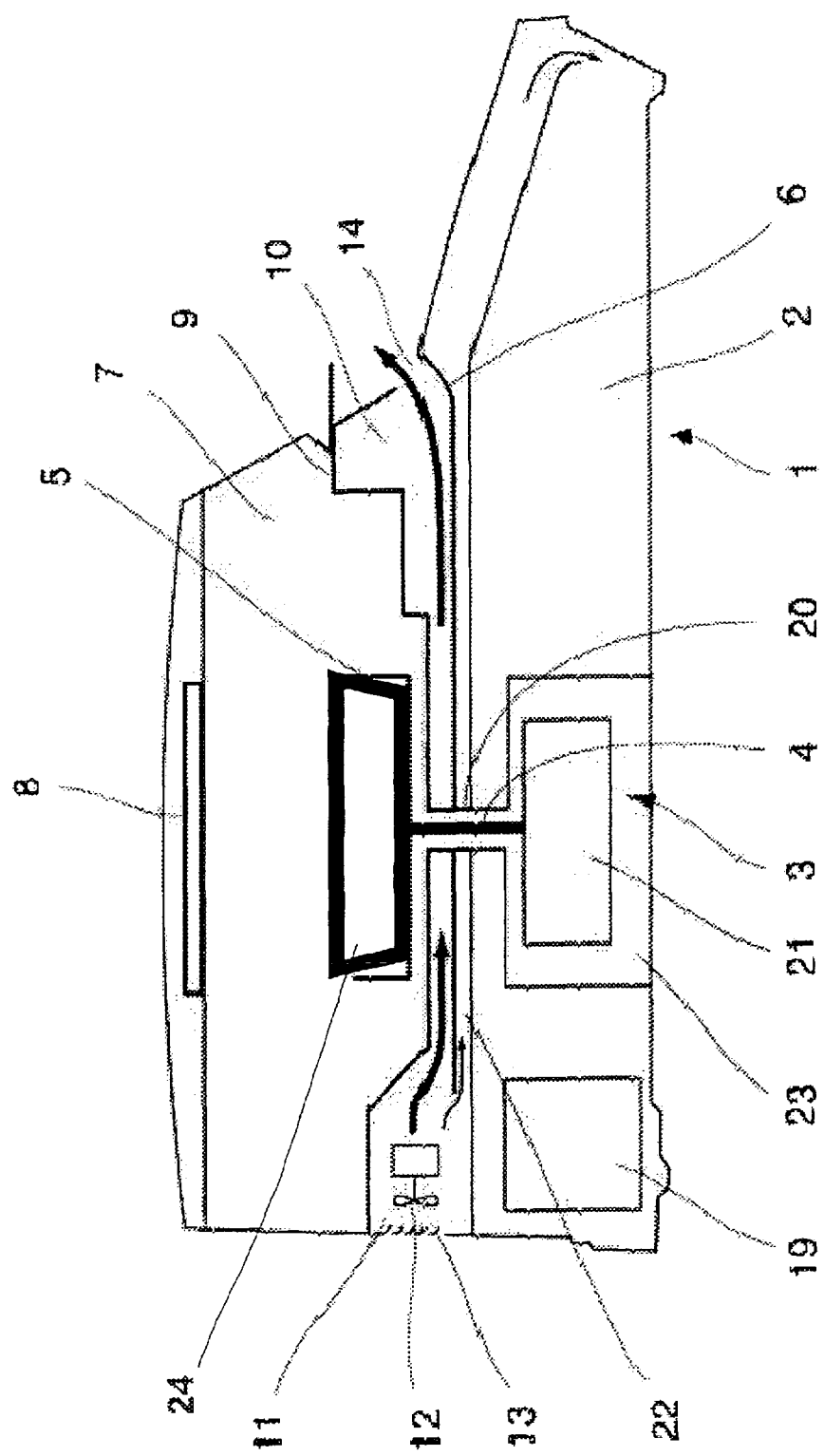
FIG. 1 represents a side view of a moisture-determination instrument with an air duct.

The moisture-determination instrument 1 of FIG. 1 has an instrument housing 2 containing a balance 3. The balance has a load-receiving connection 4 protruding through an opening in the housing 2 and supporting a removable sample tray carrier 5. A plate 6 covers the top of the instrument housing 2 except for an opening in the rear portion of the housing. The pass-through collar 20 for the load-receiving connection 4 through the plate 6 is sealed so that air and dust from the air duct cannot penetrate the areas of the weighing cell 21 and the sample tray carrier 5. The weighing cell 21 has its own enclosed compartment 23, which is sealed against dust and air from the outside. Integrated in the tilt-up cover 7 is a radiant heater 8 to heat-dry the samples that are placed on a sample tray and whose moisture content is to be determined. When the tilt-up cover 7 is closed, its side walls adjoin the plate 6 substantially over its full length and thereby close off the interior space of the moisture-determination instrument. The plate 6 and an upper shell 9 over the top of the housing 2 together form an air duct 10 that extends substantially over the entire width and length of the plate 6. The load-receiving connection 4 traverses the air duct. The rear portion of the air duct 10 is expanded upwards to form an intake compartment 11 where a fan 12 pulls in ambient air through an intake opening 13. After passing through the air duct 10, the air exits from the instrument preferably through a front opening 14 of the air duct.

The air duct may branch off into an additional channel 22, e.g., in the rear part of the duct, where a part of the air stream flows through an opening in the plate 6 and through the branch channel to cool the electronic portion 19 of the instrument.

Figure 2:
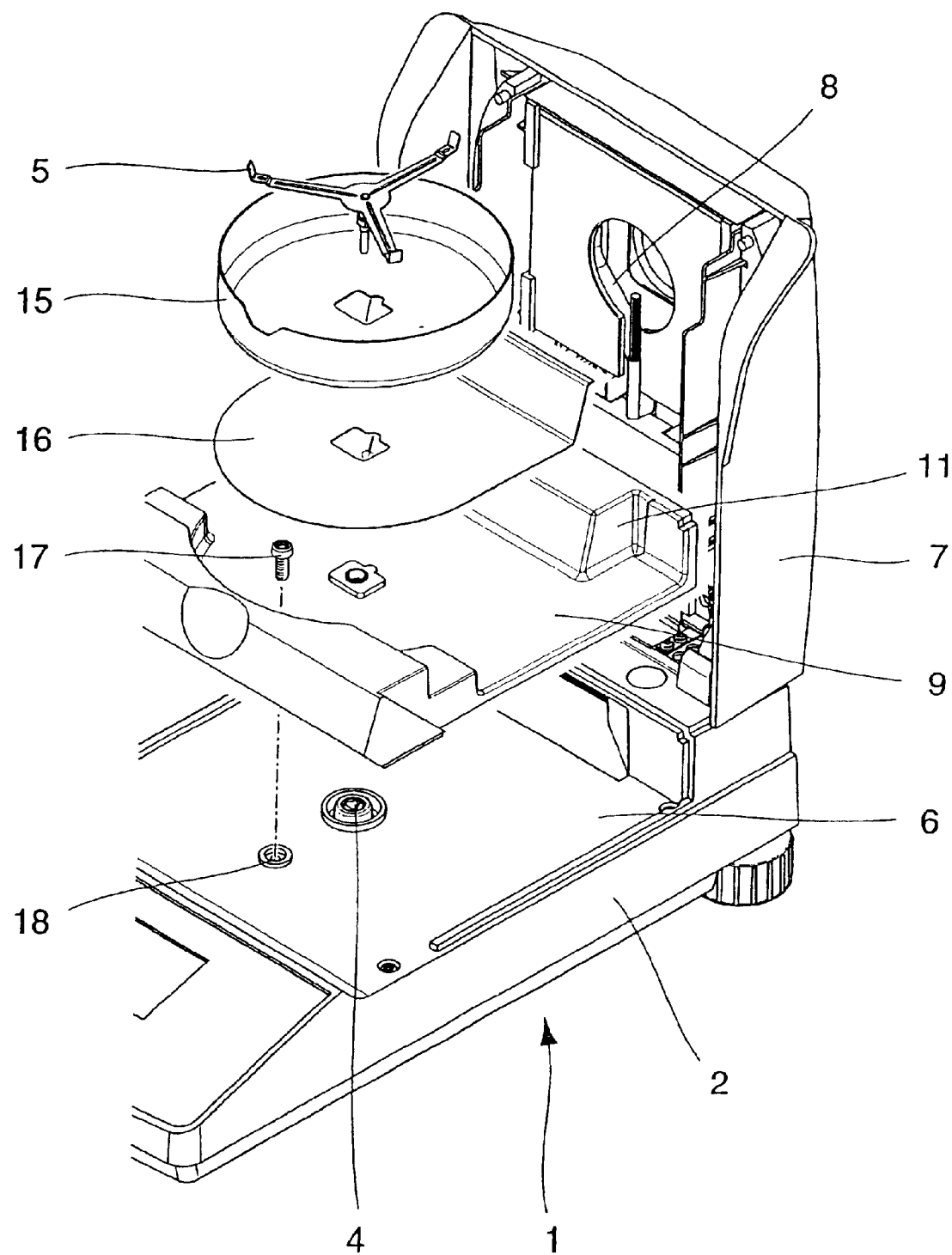
FIG. 2 represents in a three-dimensional exploded view, illustrating how the upper shell of the air duct can be taken off for cleaning.

FIG. 2 illustrates how the moisture-determination instrument is designed to facilitate the disassembly of the air duct. The cover 7 is mounted on hinges so that it can be tilted up for setting a sample on the sample tray carrier 5. To clean the instrument the cover is likewise tilted up from the instrument housing. Due to the advantageous design of the upper shell 9 and the way in which it is set on top of the instrument housing 2, dirt particles on top of the upper shell can easily be swept off to the sides, as there are no side walls standing in the way.

To clean the air duct 10, the cover 7 is opened and the sample tray carrier 5, draft shield 15 and heat shield 16 are removed, all of which requires no tools. The upper shell 9 can be taken off after the screw 17 has been removed from the threaded hole 18, using a standard screwdriver. The plate 6, which forms the bottom of the air duct is easily cleaned, e.g., by wiping with a cloth.

The upper shell 9 of the air duct can also be designed in other shapes and arrangements, for example hinged at the back so that it tilts open, or as a pull-out part that slides forward in guide rails arranged on the sides of the instrument housing 2.

Instead of being enclosed by the plate 6 and upper shell 9, the air duct can also be designed as an integral, one-piece unit that can be taken out of the instrument in its entirety. In this case, the duct can be rinsed with a fluid or blasted clean with a jet of compressed air.

In a different embodiment, the air duct is not limited to a horizontally extending chamber between the upper shell 9 and the top of the instrument housing 2, but also reaches downward over the sides of the instrument housing 2, as an inverted U-profile. As in the previously discussed embodiments of the invention, the ambient air is pulled into an air-intake compartment 11 with a fan 12 at the rear of the instrument. After passing through the air duct 10, the air exits from the instrument preferably through a front opening 14 of the air duct. With the U-profiled duct configuration, the air duct 10 takes the form of a wrap-around cover that encloses the top as well as the flanks of the instrument housing 2, attached by an easily releasable fastener as in the preceding embodiments.

It is self-evident that an easily removable air duct according to the different embodiments of the invention as described herein could also be used for other kinds of gravimetric moisture-determination instruments, e.g., for one of the instrument types representing the state of the art as described herein at the beginning. The important factor in all cases is the ease of dismantling or removing the air duct for cleaning.

What is claimed is:

1. A measuring instrument for gravimetrically determining a moisture content of a sample, comprising an instrument housing, a balance with a weighing cell installed in the instrument housing, a tray carrier mounted on the weighing cell to hold a sample on a sample tray, a source of radiant heat arranged above the sample tray, and means for conducting a stream of air between the sample tray and the weighing cell, said means comprising an air duct; said radiant heat drying the sample and thereby causing the latter to lose weight; the balance being operable to monitor said weight loss and to therefrom determine the moisture content of the sample; wherein the air duct comprises an upper shell, which forms only an upper wall of the air duct and is configured to be detached from the instrument housing for the purpose of cleaning the air duct.

2. The measuring instrument of claim 1, wherein the measuring instrument comprises means for fastening the upper shell to the instrument housing; and wherein said means for fastening are releasable, thereby allowing the upper shell to be removed from the instrument housing.

3. The measuring instrument of claim 1, wherein the upper shell is slidably mounted so that it can be pulled off in a forward direction.

4. The measuring instrument of claim 1, wherein the air duct has a U-shaped profile, closing off the instrument housing from above as well as laterally.

5. The measuring instrument of claim 1, wherein the air duct has at least one branch channel running near an electronic portion of the measuring instrument and serving to cool said electronic portion.

6. A measuring instrument for gravimetrically determining a moisture content of a sample, comprising an instrument housing, a balance with a weighing cell installed in the instrument housing, a tray carrier mounted on the weighing cell to hold a sample on a sample tray, a source of radiant heat arranged above the sample tray, and means for conducting a stream of air between the sample tray and the weighing cell, said means comprising an air duct; said radiant heat drying the sample and
    thereby causing the latter to loose weight; the balance being operable to monitor said weight loss and to therefrom determine the moisture content of the sample; wherein the air duct comprises an upper shell mounted on top of the instrument housing and so as to form only an upper wall of the air duct that closes off the air duct from above; wherein the upper shell is hinged to a rear portion of the instrument housing, thereby allowing the upper shell to be tilted about a horizontal axis.

7. The measuring instrument of claim 6, wherein the air duct has a U-shaped profile, closing off the instrument housing from above as well as laterally.

8. The measuring instrument of claim 6, wherein the air duct has at least one branch channel running near an electronic portion of the measuring instrument and serving to cool said electronic portion.

9. A measuring instrument for gravimetrically determining a moisture content of a sample, comprising an instrument housing, a balance with a weighing cell installed in the instrument housing, a tray carrier mounted on the weighing cell to hold a sample on a sample tray, a source of radiant heat arranged above the sample tray, and means for conducting a stream of air between the sample tray and the weighing cell, said means comprising an air duct; said radiant heat drying the sample and thereby causing the latter to lose weight; the balance being operable to monitor said weight loss and to therefrom determine the moisture content of the sample, wherein the air duct comprises a single-piece air duct unit, wherein the measuring instrument comprises means for fastening the single-piece air duct unit to the instrument housing, and wherein said means for fastening are releasable, thereby allowing the single-piece air duct unit to be removed from the instrument housing.

10. The measuring instrument of claim 9, wherein the air duct has at least one branch channel running near an electronic portion of the measuring instrument and serving to cool said electronic portion.

\* \* \* \* \*